United States Patent
Ci

(10) Patent No.: US 10,406,195 B2
(45) Date of Patent: Sep. 10, 2019

(54) SOLID DRINK FOR REGULATING PHLEGM-DAMPNESS CONSTITUTION AND PROCESSING METHOD THEREOF

(71) Applicant: Zhonghua Ci, Beijing (CN)

(72) Inventor: Zhonghua Ci, Beijing (CN)

( * ) Notice: Subject to any disclaimer, the term of this patent is extended or adjusted under 35 U.S.C. 154(b) by 0 days.

(21) Appl. No.: 15/876,224

(22) Filed: Jan. 22, 2018

(65) Prior Publication Data

US 2019/0160137 A1     May 30, 2019

(30) Foreign Application Priority Data

Nov. 30, 2017 (CN) .......................... 2017 1 1244092

(51) Int. Cl.

| | | |
|---|---|---|
| A61K 36/00 | (2006.01) | |
| A61K 36/9064 | (2006.01) | |
| A61K 36/185 | (2006.01) | |
| A61K 36/535 | (2006.01) | |
| A61K 36/31 | (2006.01) | |
| A61K 36/752 | (2006.01) | |
| A61K 36/076 | (2006.01) | |
| A61K 36/899 | (2006.01) | |
| A61K 36/532 | (2006.01) | |
| A61K 36/03 | (2006.01) | |
| A61K 36/8994 | (2006.01) | |
| A61K 47/36 | (2006.01) | |
| A61K 47/18 | (2017.01) | |
| A61K 9/00 | (2006.01) | |
| A23L 2/39 | (2006.01) | |
| A23L 2/60 | (2006.01) | |
| A23L 33/105 | (2016.01) | |
| A23L 33/125 | (2016.01) | |
| A61K 36/488 | (2006.01) | |

(52) U.S. Cl.
CPC ............ *A61K 36/9064* (2013.01); *A23L 2/39* (2013.01); *A23L 2/60* (2013.01); *A23L 33/105* (2016.08); *A23L 33/125* (2016.08); *A61K 9/0095* (2013.01); *A61K 36/03* (2013.01); *A61K 36/076* (2013.01); *A61K 36/185* (2013.01); *A61K 36/31* (2013.01); *A61K 36/488* (2013.01); *A61K 36/532* (2013.01); *A61K 36/535* (2013.01); *A61K 36/752* (2013.01); *A61K 36/899* (2013.01); *A61K 36/8994* (2013.01); *A61K 47/183* (2013.01); *A61K 47/36* (2013.01); *A23V 2002/00* (2013.01); *A61K 2236/15* (2013.01)

(58) Field of Classification Search
None
See application file for complete search history.

*Primary Examiner* — Qiuwen Mi
(74) *Attorney, Agent, or Firm* — Gokalp Bayramoglu

(57) ABSTRACT

A solid drink includes the following components of raw materials in parts by weight: kudzu vine root 25-60 parts, nutmeg 13-35 parts, fructus perillae 30-50 parts, radish seed 34-53 parts, dried tangerine peel 28-55 parts, poria 27-52 parts, fructus amomi 4-15 parts, malt 26-50 parts, *agastache rugosa* 14-33 parts, kelp 24-51 parts, semen coicis 22-40 parts, dextrin 50-90 parts, maltodextrin 38-70 parts, soluble starch 35-70 parts, and aspartame 0.1-0.5 parts.

10 Claims, 1 Drawing Sheet

SOLID DRINK FOR REGULATING PHLEGM-DAMPNESS CONSTITUTION AND PROCESSING METHOD THEREOF

CROSS REFERENCE TO RELATED APPLICATIONS

This application is based upon and claims priority to Chinese patent application no. CN2017112440928, filed on Nov. 30, 2017, the entire content of which is incorporated herein by reference.

TECHNICAL FIELD

The present invention relates to the field of health food, and particularly to a solid drink for regulating phlegm-dampness constitution and a processing method thereof.

BACKGROUND

According to "Classification and Determination of Constitution in TCM" by China Association of Chinese Medicine, the constitution of human bodies includes nine types, namely, balanced constitution (constitution of yin-yang harmony), phlegm-dampness constitution, yin-deficiency constitution, qi (vital energy)-deficiency constitution, phlegm-dampness (tanshi) constitution, dampness-heat constitution, qi-depression constitution, blood-stasis constitution, and allergic (special, tebing) constitution. Most of them belong to sub-health status.

The phlegm-dampness constitution manifests phlegm-dampness retention caused by phlegm formation due to dampness accumulation when the functions of internal organs (zang and fu) of the human body dysfunction, which easily leads to disordered transportation and transformation of qi (vital energy)-blood and body fluid, and water and dampness stagnation, usually showing obesity, fat abdomen, chest distress, excessive phlegm, drowsiness liability, heavy body and unpleasantness, addiction to greasy food and pure liquor, swelling tongue, and white greasy tongue fur, and is mostly caused by invasion of coldness and dampness, improper diet, inborn endowment, oldness and long illness, and lack of exercises, with different symptoms usually due to different parts of the phlegm-dampness retention. When being attacked, the phlegm-dampness patients tend to develop diabetes, stroke, chest obstruction and so on, with poor adaptability to plum rains and damp environments. An important treatment is eliminating dampness and phlegm, together with balancing and improving the phlegm-dampness constitution to prevent occurrence of the phlegm-dampness diseases.

The phlegm-dampness constitution, being a sub-health constitution, belongs to chronic conditions with a relatively long course, and requires long-term administration and gradual regulation so as to achieve the effects of eliminating dampness and phlegm. The common Chinese medicine dosage form includes decoction and Chinese patent drug such as pills. The decoction has a better efficacy, but is tedious to take, and the taste thereof is also bad. It is not easy for patients to persistently take decoction for a long period of time, while the efficacy of pills is relatively poor.

Food is the best for preventing diseases and keeping healthy for human beings. "Homology between medicine and food" is one of the most valuable contributions of original Chinese medical science to the human beings. According to "Rites of Zhou•Tianguan•Curing Sickness", curing diseases by combining five tastes, five cereals, and five medicines, which indicates the physiological health-care function of food. A method of regulating organism using properties of food to get healthy or cure diseases is called as food therapy (nutrition therapy, dietary therapy). However, "nourishment" is better than "therapy". Dietary nourishment refers to nourishing by combining nutritional effects of food with the physical condition of the body to enhance resistibility and immunity, and further to prolong life and have a strong physique. According to "Qian Jin Prescriptions", a doctor should firstly know the source of a disease and symptoms, then treat the disease with corresponding food. If the disease cannot be cured through food therapy, then a medicine is used. It can be seen that the application of food therapy is not only the basic treatment means of doctors at that time, but also an important ground for evaluating whether a doctor has excellent medical skills.

It is proposed in "Huangdi Neijing" that "making preventive treatment before getting illness is the top-class medical skill, performing treatment when illness is suspected is the middle-class medical skill, and performing treatment when illness is present is the lower-class medical skill". "Making preventive treatment before getting illness" refers to taking corresponding measures to prevent occurrence and development of illness. The constitution determines our health and susceptibility to diseases. In the face of various diseases, increasingly low morbidity age, and more and more sub-healthy population, the food therapy is favored by more and more consumers due to its advantages of being healthy and natural. With regard to problems easily arising, it is of critical significance to develop a type of food having the function of maintaining good health and regulating phlegm-dampness constitution with good taste by combining the precious experience of traditional Chinese health care and accumulation of good aspects of keeping the balanced constitution of the traditional Chinese medicine, using technologies and methods of modern sciences, based on the homology between medicine and food.

SUMMARY

A main object of the present invention is to provide a health-care food for regulating phlegm-dampness constitution.

In order to achieve the above object, according to one aspect of the present invention, a solid drink for regulating phlegm-dampness constitution is provided.

The solid drink for regulating phlegm-dampness constitution according to the present invention includes the following components of raw materials in parts by weight: kudzu vine root 25-60 parts, nutmeg 13-35 parts, fructus perillae 30-50 parts, radish seed 34-53 parts, dried tangerine peel 28-55 parts, poria 27-52 parts, fructus amomi 4-15 parts, malt 26-50 parts, *agastache rugosa* 14-33 parts, kelp 24-51 parts, semen coicis 22-40 parts, dextrin 50-90 parts, maltodextrin 38-70 parts, soluble starch 35-70 parts, and aspartame 0.1-0.5 parts.

Furthermore, the solid drink for regulating phlegm-dampness constitution of the present invention includes the following components of raw materials in parts by weight: kudzu vine root 30-50 parts, nutmeg 18-30 parts, fructus perillae 35-45 parts, radish seed 37-49 parts, dried tangerine peel 33-46 parts, poria 33-45 parts, fructus amomi 6-11 parts, malt 32-46 parts, *agastache rugosa* 17-29 parts, kelp 31-47 parts, semen coicis 29-36 parts, dextrin 60-80 parts, maltodextrin 45-63 parts, soluble starch 45-63 parts, and aspartame 0.2-0.4 parts.

Furthermore, the solid drink for regulating phlegm-dampness constitution of the present invention includes the following components of raw materials in parts by weight: kudzu vine root 40 parts, nutmeg 24 parts, fructus perillae 40 parts, radish seed 40 parts, dried tangerine peel 40 parts, poria 40 parts, fructus amomi 8 parts, malt 40 parts, *agastache rugosa* 24 parts, kelp 40 parts, semen coicis 40 parts, dextrin 68 parts, maltodextrin 51 parts, soluble starch 51 parts, and aspartame 0.3 parts.

In order to achieve the above object, according to another aspect of the present invention, a method for processing a solid drink for regulating phlegm-dampness constitution is provided.

The method for processing a solid drink for regulating phlegm-dampness constitution according to the present invention includes the following steps:

(1) preparing raw materials: mixing kudzu vine root, dried tangerine peel, fructus perillae, radish seed, kelp, poria, malt, semen coicis, nutmeg, *agastache rugosa*, and fructus amomi having undergone purification, cleansing, cutting, and grinding, for subsequent use;

(2) decocting: decocting twice a mixture obtained in step (1) with addition of water, to obtain a Chinese medicine liquid;

(3) concentrating: feeding the Chinese medicine liquid obtained in step (2) into a concentrator via a pipeline, to be concentrated into a thick paste;

(4) wet granulating: mixing and stirring dextrin, maltodextrin, soluble starch, and aspartame to obtain a mixed excipient, and adding the thick paste obtained in step (3) to the mixed excipient, then stirring and granulating them.

Furthermore, operations of the twice decocting processes in the above step (2) are as follows:

for the first time, adding water of 10 times the weight of the mixture obtained in the above step (1), heating them for decocting and extracting the same, wherein timing is started when they are boiling, and after 1.5 hours of decoction and extraction, immediately feeding a medicine liquid through a pipeline filter by a pump into a stainless steel medicine liquid tank;

for the second time, adding water of 8 times the weight of the mixture obtained in the above step (1), heating them for decocting and extracting the same, wherein timing is started when they are boiling, and after 1.5 hours of decoction and extraction, immediately feeding the medicine liquid through the pipeline filter by the pump into the stainless steel medicine liquid tank, and mixing it evenly with the medicine liquid obtained from the first time of decoction and extraction.

Furthermore, the concentration temperature in the above step (3) is 70-80° C., and the relative density of the resulted thick paste is 1.2-1.5 under a temperature condition of 50° C.

Furthermore, the wet granulating in the above step (4) includes the following steps:

(4.1) dry blending: putting dextrin, maltodextrin, soluble starch, and aspartame into an efficient mixing granulator to be mixed and stirred for 15 minutes, to obtain the mixed excipient;

(4.2) sizing for the first time: adding the thick paste extracted in step (3) gradually to the mixed excipient, mixing and stirring the thick paste at cutting speed I and stirring speed I to granulate them to obtain a soft material, and sizing the soft material for the first time;

(4.3) drying: putting the sized particles obtained in step (4.2) into a boiling dryer to be dried;

(4.4) sizing for the second time: performing the second time of sizing by an oscillating machine.

Furthermore, a 12-mesh screen is used in the first time of sizing, and a 10-mesh screen is used in the second time of sizing.

Furthermore, in the drying process of step (4.3), a temperature of the materials is kept at 70-80° C., and a moisture of the final materials is kept below 5%.

Furthermore, a step of selecting particles is further included after the second time of sizing, to select particles with 10-60 meshes.

The solid drink of the present invention is easy to manufacture, and all the raw materials used are medicine materials of medicinal and edible dual purposes, and all the excipients used also satisfy national standard GB2760-2011 (National Food Safety Standard for Uses of Food Additives). It is safe to eat (drink) with good taste, and has certain effects on improving the phlegm-dampness constitution. Moreover, the processing process is suitable for industrial mass production.

BRIEF DESCRIPTION OF THE DRAWINGS

The figures constituting a portion of the present application are used for further understanding of the present invention, so as to make it more obvious other features, objects, and advantages of the present application. Exemplary examples of the present application, drawings, and description thereof are used to explain the present invention, rather than improperly limiting the present invention. In the figures.

DETAILED DESCRIPTION OF THE EMBODIMENTS

Figure 1:
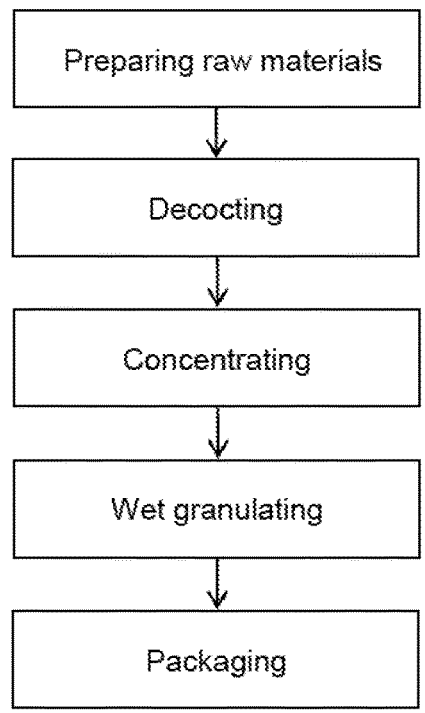
FIG. 1 shows a processing process of a solid drink according to an example of the present invention.

In order to make a person skilled in the art better understand solutions of the present application, below technical solutions of the examples of the present application will be described clearly and completely in conjunction with figures of the examples of the present application. Apparently, some but not all of examples of the present application are described. Based on the examples of the present application, all the other examples, which a person ordinarily skilled in the art obtains without paying inventive effort, fall within the scope of protection of the present application.

Besides, the term "include (comprise)" and any variants thereof are intended to cover non-exclusive containing, for example, a product including a series of raw materials or a method including a series of steps is not necessarily limited to listing those raw materials or steps, but may include other steps or raw materials which are not clearly listed or inherent to the method or product.

It should be indicated that examples of the present application and features in the examples can be combined with each other without conflict. The present application will be described in detail with reference to the figures in conjunction with the examples.

A main object of the present invention is to provide a health-care food for regulating phlegm-dampness constitution.

In order to realize the above object, according to one aspect of the present invention, a solid drink for regulating phlegm-dampness constitution is provided.

The solid drink for regulating phlegm-dampness constitution according to the present invention includes the following components of raw materials in parts by weight: kudzu vine root 25-60 parts, nutmeg 13-35 parts, fructus perillae 30-50 parts, radish seed 34-53 parts, dried tangerine peel 28-55 parts, poria 27-52 parts, fructus amomi 4-15 parts, malt 26-50 parts, *agastache rugosa* 14-33 parts, kelp 24-51 parts, semen coicis 22-40 parts, dextrin 50-90 parts, maltodextrin 38-70 parts, soluble starch 35-70 parts, and aspartame 0.1-0.5 parts.

Kudzu vine root: kudzu vine root, sweet and acrid in taste and cold in nature, exerts the curative effect through the lung and stomach channels, relieves the muscles and skin and allay fever, promotes eruption, generates the body fluid and quenches thirst, invigorates yang and cures diarrhea, and is used for treatment of syndrome of fever, sever back pain, measles without adequate eruption, thirst caused by fever, yin-deficiency diabetes, heat diarrhea, and spleen-deficiency diarrhea.

Nutmeg: nutmeg, acrid in taste and warm in nature, exerts the curative effect through the spleen, stomach, and large intestine channels, warns the middle energizer to promote the circulation of qi, astringes intestine to cure diarrhea, and is used for treatment of deficient cold of spleen and stomach, chromatic diarrhea, abdominal distention, reduced appetite and vomiting.

Fructus perillae: fructus perillae, acrid in taste, warm in nature, and non-toxic, exerts the curative effect through the lung and large intestine channels, has the efficacy of descending qi, clearing phlegm, moistening the lungs, and widening intestine, and mainly cures choking cough, phlegmdyspnea, qi stagnation, astriction, and qi depression caused by cold air and wet wind in waist and feet.

Radish seed: radish seed, mild in nature, acrid and sweet in taste, exerts the curative effect through the lung, spleen, and stomach channels, promotes digestion, eliminates flatulence, descends qi, and eliminates phlegm, and is used for treatment of fullness with food stagnation, abdominal distention, constipation, indigestion diarrhea, phlegm obstruction cough and asthma.

Dried tangerine peel: dried tangerine peel, acrid and bitter in taste, mild in nature, exerts the curative effect through the lung and spleen channels, regulates qi and the middle energizer, eliminates dampness and phlegm, and is used for treatment of cough with abundance of phlegm, indigestion, liquor damage, nausea and oppression in the abdomen.

Poria: poria, sweet and light in taste, and mild in nature, exerts the curative effect through the heart, lung, spleen, and kidney channels, moistens dryness and promotes diuresis, tonifies the spleens, and calms the heart, and is used for treatment of edema and oliguria, phlegm-fluid retention, reduced spleen-deficiency appetite, loose stool diarrhea, unease, and palpitation and insomnia.

Fructus amomi: fructus amomi, acrid in taste and damp in nature, exerts the curative effect through the spleen, stomach, and lung channels, has the efficacy of eliminating dampness, stimulating appetite, warming the spleen, arresting diarrhea, regulating qi and preventing miscarriage, and is used for treatment of turbid dampness retention, stuffy abdomen without hunger, deficient cold of spleen and stomach, vomiting, diarrhea, pernicious vomiting, and fetal irritability.

Malt: malt, sweet in taste and mild in nature, exerts the curative effect through the spleen and stomach channels, promotes the circulation of qi and digestion, tonifies the spleens, stimulates appetite, terminates lactation, and relieves flatulence, and is used for treatment of indigestion, abdominal distention, reduced spleen-deficiency appetite, milk stasis, breast tenderness, delectation of women, liver depression and hypochondriac pain, and stomachache due to emotional depression and the hyperactive liver-qi attacking the stomach.

*Agastache rugosa*: *agastache rugosa*, the whole plant of which is used as drug, acrid in taste and mild in nature, exerts the curative effect through the spleen, stomach, and lung channels, eliminates dampness, refreshes the spleen, repels foulness, regulates the middle warmer, relieves summer-heat, and relieves exterior syndrome by diaphoresis, and is used for treatment of syndromes such as dampness obstruction in spleen and stomach, abdominal distention, beginning of damp-warm syndrome, vomiting, diarrhea, summer-heat dampness, fever with cold aversion, aversion to cold with fever, and chest and gastral cavity nausea.

Kelp: kelp, salty in taste and cold in nature, exerts the curative effect through the liver, stomach, and kidney channels, dissolves phlegm, softens hard masses, resolves hard lump, moistens dryness and relieves swelling, and is used for treatment of thyroid tumor, scrofula, testicular swelling and pain, phlegm-fluid retention edema.

Semen coicis: semen coicis, sweet and light in taste and cold in nature, exerts the curative effect through the spleen, stomach, and lung channels, has the functions of moistening dryness and promoting diuresis, tonifying the spleens, curing diarrhea, eliminating arthralgia syndromes, discharging pus, and is used for treatment of edema, beriberi, difficult urination, spleen-deficiency diarrhea, dampness arthralgia muscular constriction, pulmonary abscess, intestinal carbuncle, excrescence, cancerous protuberance.

The phlegm-dampness constitution is featured by obesity, fat and soft abdomen, yellowish complexion and edema, excessive sticky sweating, thick and greasy tongue fur, drowsiness liability, heavy body and unpleasantness. The regulation and treatment of the phlegm-dampness constitution should be based on the principle of eliminating dampness and phlegm, dissipating dampness and nursing the body, and promote the rising of clear yang qi, and enable healthy transportation of the spleen and stomach so as to transport water and dampness. In the prescription, the dried tangerine peel regulates qi and the middle energizer, and eliminates dampness and phlegm, the kudzu vine root relieves the muscles and skin and allays fever, generates the body fluid and quenches thirst, invigorates yang and cures diarrhea, the nutmeg regulates qi and the middle energizer, dries the cold-dampness, and relieves alcoholism, the semen coicis mainly treats dampness arthralgia, benefits intestines and stomach, alleviates heat and relieves summer heat due to the cold nature, the fructus perillae descends qi, clears phlegm, relieves asthma, and lubricates the intestines, the radish seed promotes digestion, eliminates flatulence, and benefits qi reinforcement, the kelp removes stasis, eliminates phlegm, regulates qi, and resolves hard lump, the poria moistens dryness and promotes diuresis, tonifies the spleens, and calms the heart, the fructus amomi refreshes the spleen, dries dampness, promotes the circulation of qi, regulates the middle energizer, and harmonizes stomach, the malt promotes the circulation of qi and digestion, tonifies the spleens, stimulates appetite, terminates lactation, and relieves flatulence, the *agastache rugosa* eliminates dampness, refreshes the spleen, repels foulness, regulates the middle warmer, relieves summer-heat, relieves exterior syndrome by diaphoresis. By using these drugs in combination, san jiao (triple energizer) is thoroughly smoothed and regulated, qi and blood are transported, both the interior and the exterior are treated, excessive phlegm, water, dampness, and stagnation are eliminated, thus the phlegm-dampness constitution is improved, further the object of losing weight is achieved.

As shown in FIG. 1, a method for processing a solid drink for regulating phlegm-dampness constitution includes the following steps:

(1) preparing raw materials: mixing kudzu vine root, dried tangerine peel, fructus perillae, radish seed, kelp, poria, malt, semen coicis, nutmeg, *agastache rugosa*, and fructus amomi having undergone purification, cleansing, cutting, and grinding, for subsequent use, with proportions of respective raw materials being the proportions provided in the present invention;

(2) decocting: decocting twice a mixture obtained in step (1) with addition of water, to obtain a Chinese medicine liquid;

(3) concentrating: feeding the Chinese medicine liquid obtained in step (2) into a concentrator via a pipeline, to be concentrated into a thick paste;

(4) wet granulating: mixing and stirring dextrin, maltodextrin, soluble starch, and aspartame to obtain a mixed excipient, and adding the thick paste obtained in step (3) to the mixed excipient, then stirring and granulating them;

(5) packaging: subjecting a product obtained after the wet granulating to a packaging step, to result in a finished product.

The object of step (1) is to remove fat from the seed Chinese medicine materials ground with a 2-mesh screen; cutting or grinding rhizomatic Chinese medicine materials, enriched in cellulose and starch, to be extracted can effectively reserve target ingredients and prevent expansion of polysaccharides; purification can remove impurities and soil, and effectively reduce remnant of pollutants such as heavy metals and pesticides.

Operations of the twice decocting processes in the above step (2) are as follows: for the first time, adding water of 10 times the weight of the mixture obtained in the step (1), heating them for decocting and extracting the same, wherein timing is started when they are boiling, and after 1.5 hours of decoction and extraction, immediately feeding the medicine liquid through a pipeline filter by a pump into a stainless steel medicine liquid tank;

for the second time, adding water of 8 times the weight of the mixture obtained in the step (1), heating them for decocting and extracting the same, wherein timing is started when they are boiling, and after 1.5 hours of decoction and extraction, immediately feeding the medicine liquid through the pipeline filter by the pump into the stainless steel medicine liquid tank, and mixing it evenly with the medicine liquid obtained from the first time of decoction and extraction.

The concentration temperature in the above step (3) is 70-80° C., and the relative density of the resulted thick paste is 1.2-1.5 under the temperature condition of 50° C. Low-temperature evaporation can effectively reduce decomposition of heat-sensitive components, for example, organic acids such as citric acid, malic acid, and oxalic acid, moreover, it has high concentration efficiency with no discharge of solvent vapor, and facilitates evaporation and airtightness without polluting environment.

Figure 2:
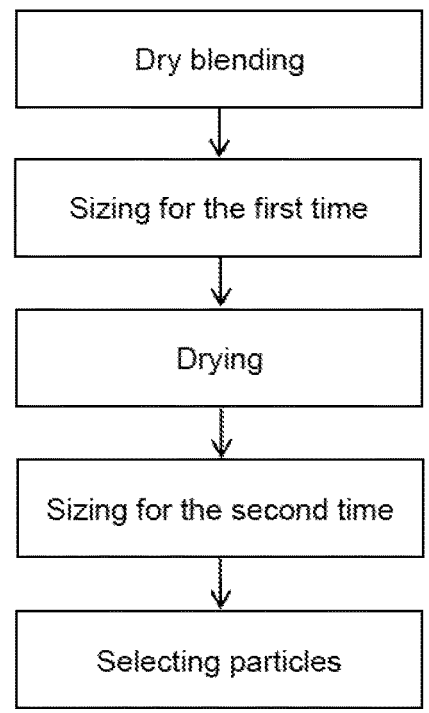
FIG. 2 shows specific steps of wet granulating in a processing process of a solid drink according to an example of the present invention.

As shown in FIG. 2, the wet granulating in the above step (4) includes the following steps:

(4.1) dry blending: putting dextrin, maltodextrin, soluble starch, and aspartame into an efficient mixing granulator to be mixed and stirred for 15 minutes, to obtain the mixed excipient, with proportions of respective raw materials being the proportions provided in the present invention;

(4.2) sizing for the first time: adding the thick paste extracted in step (3) gradually to the mixed excipient, mixing and stirring the thick paste at cutting speed I and stirring speed I to granulate them to obtain a soft material, and sizing the soft material for the first time, wherein mixing granulation can preferably prevent separation of various components, and since the segregation phenomenon easily occurs due to differences existing among particle sizes and densities of the components of the mixed extract, the granulation not only can overcome this problem, but also can significantly improve the solubility;

(4.3) drying: putting the sized particles obtained in step (4.2) into a boiling dryer to be dried, wherein the boiling dryer can effectively control the particle size distribution, and control the moisture of the product:

(4.4) sizing for the second time: performing the second time of sizing by an oscillating machine, wherein through the second time of sizing, the particles distribution, bulk density, and compactness can be controlled.

In the above steps, a 12-mesh screen is used in the first time of sizing, and a 10-mesh screen is used in the second time of sizing.

In the drying process of the above step (4.3), the temperature of the materials is kept at 70-80° C., and the moisture of the final materials is kept below 5%. In the present step, a pot can be turned frequently according to the drying situation of the materials, ensuring that the moisture of the final materials meets requirements.

On the basis of the above embodiment, a step of selecting particles is further included after the second time of sizing, to select particles with 10-60 meshes. The appearance and homogeneity of the product particles can be improved by selecting the particles. In practical operation, after the particle selection, a product name, a product lot number, specification, net weight, date of manufacture, name of position, and person in charge are recorded and tagged, and a delivery receipt is filled in, then the product is transferred to an intermediate station.

EXAMPLE 1

A solid drink for regulating phlegm-dampness constitution included the following components of raw materials in parts by weight: kudzu vine root 25 parts, nutmeg 13 parts, fructus perillae 30 parts, radish seed 34 parts, dried tangerine peel 28 parts, poria 27 parts, fructus amomi 4 parts, malt 26 parts, *agastache rugosa* 14 parts, kelp 24 parts, semen coicis 22 parts, dextrin 50 parts, maltodextrin 38 parts, soluble starch 35 parts, and aspartame 0.1 part.

A preparing method was as follows:

(1) preparing raw materials: mixing kudzu vine root, dried tangerine peel, fructus perillae, radish seed, kelp, poria, malt, semen coicis, nutmeg, *agastache rugosa*, and fructus amomi having undergone purification, cleansing, cutting, and grinding, for subsequent use;

(2) decocting: decocting twice a mixture obtained in step (1) with addition of water, to obtain a Chinese medicine liquid, operations of the twice decocting processes being as follows:

for the first time, adding water of 10 times the weight of the mixture obtained in the step (1), heating them for decocting and extracting the same, wherein timing was started when they were boiling, and after 1.5 hours of decoction and extraction, immediately feeding the medicine liquid through a pipeline filter by a pump into a stainless steel medicine liquid tank:

for the second time, adding water of 8 times the weight of the mixture obtained in the step (1), heating them for decocting and extracting the same, wherein timing was started when they were boiling, and after 1.5 hours of decoction and extraction, immediately feeding the medicine liquid through the pipeline filter by the pump into the stainless steel medicine liquid tank, and mixing it evenly with the medicine liquid obtained from the first time of decoction and extraction;

(3) concentrating: feeding the Chinese medicine liquid obtained in step (2) into a concentrator via a pipeline, to be concentrated into a thick paste, the concentration temperature being 70° C., and the relative density of the resulted thick paste being 1.2 under the temperature condition of 50° C.;

(4) wet granulating:

(4.1) dry blending: putting dextrin, maltodextrin, soluble starch, and aspartame into an efficient mixing granulator to be mixed and stirred for 15 minutes, to obtain a mixed excipient;

(4.2) sizing for the first time: adding the thick paste extracted in step (3) gradually to the mixed excipient, mixing and stirring the thick paste at cutting speed I and stirring speed I to granulate them to obtain a soft material, and sizing the soft material for the first time with a 12-mesh screen:

(4.3) drying: putting the sized particles obtained in step (4.2) into a boiling dryer to be dried, the temperature of the materials being kept at 70° C., and the moisture of the final materials being kept at 5%; (4.4) sizing for the second time: performing the second time of sizing by an oscillating machine with a 10-mesh screen;

(4.5) selecting particles: selecting particles with 10-60 meshes;

(5) packaging: bagging mixed qualified particles according to standard operation instructions of an automatic packaging machine, wherein packaging appearance and quantity was detected at any time, and adjustment was made in time in case of abnormalities, closing and storing the packaged particles in a clean container, with a product name, a lot number, quantity, date, etc. being marked for subsequent use, wherein a reference packaging quantity was 8 g per bag, and a packaging quantity limit was 8 g per bag ±5%.

EXAMPLE 2

A solid drink for regulating phlegm-dampness constitution included the following components of raw materials in parts by weight: kudzu vine root 60 parts, nutmeg 35 parts, fructus perillae 50 parts, radish seed 53 parts, dried tangerine peel 55 parts, poria 52 parts, fructus amomi 15 parts, malt 50 parts, *agastache rugosa* 33 parts, kelp 51 parts, semen coicis 40 parts, dextrin 90 parts, maltodextrin 70 parts, soluble starch 70 parts, and aspartame 0.5 parts.

A preparing method was as follows:

(1) preparing raw materials: mixing kudzu vine root, dried tangerine peel, fructus perillae, radish seed, kelp, poria, malt, semen coicis, nutmeg, *agastache rugosa*, and fructus amomi having undergone purification, cleansing, cutting, and grinding, for subsequent use;

(2) decocting: decocting twice a mixture obtained in step (1) with addition of water, to obtain a Chinese medicine liquid, operations of the twice decocting processes being as follows:

for the first time, adding water of 10 times the weight of the mixture obtained in the step (1), heating them for decocting and extracting the same, wherein timing was started when they were boiling, and after 1.5 hours of decoction and extraction, immediately feeding the medicine liquid through a pipeline filter by a pump into a stainless steel medicine liquid tank;

for the second time, adding water of 8 times the weight of the mixture obtained in the step (1), heating them for decocting and extracting the same, wherein timing was started when they were boiling, and after 1.5 hours of decoction and extraction, immediately feeding the medicine liquid through the pipeline filter by the pump into the stainless steel medicine liquid tank, and mixing it evenly with the medicine liquid obtained from the first time of decoction and extraction;

(3) concentrating: feeding the Chinese medicine liquid obtained in step (2) into a concentrator via a pipeline, to be concentrated into a thick paste, the concentration temperature being 80° C., and the relative density of the resulted thick paste being 1.5 under the temperature condition of 50° C.;

(4) wet granulating:

(4.1) dry blending: putting dextrin, maltodextrin, soluble starch, and aspartame into an efficient mixing granulator to be mixed and stirred for 15 minutes, to obtain a mixed excipient:

(4.2) sizing for the first time: adding the thick paste extracted in step (3) gradually to the mixed excipient, mixing and stirring the thick paste at cutting speed I and stirring speed I to granulate them to obtain a soft material, and sizing the soft material for the first time with a 12-mesh screen;

(4.3) drying: putting the sized particles obtained in step (4.2) into a boiling dryer to be dried, the temperature of the materials being kept at 80° C., and the moisture of the final materials being kept at 3%; (4.4) sizing for the second time: performing the second time of sizing by an oscillating machine with a 10-mesh screen:

(4.5) selecting particles: selecting particles with 10-60 meshes;

(5) packaging: bagging mixed qualified particles according to standard operation instructions of an automatic packaging machine, wherein packaging appearance and quantity was detected at any time, and adjustment was made in time in case of abnormalities, closing and storing the packaged particles in a clean container, with a product name, a lot number, quantity, date, etc. being marked for subsequent use, wherein a reference packaging quantity was 8 g per bag, and a packaging quantity limit was 8 g per bag ±5%.

EXAMPLE 3

A solid drink for regulating phlegm-dampness constitution included the following components of raw materials in parts by weight: kudzu vine root 30 parts, nutmeg 18 parts, fructus perillae 35 parts, radish seed 37 parts, dried tangerine peel 33 parts, poria 33 parts, fructus amomi 6 parts, malt 32 parts, *agastache rugosa* 17 parts, kelp 31 parts, semen coicis 29 parts, dextrin 60 parts, maltodextrin 45 parts, soluble starch 45 parts, and aspartame 0.2 parts.

A preparing method was as follows:

(1) preparing raw materials: mixing kudzu vine root, dried tangerine peel, fructus perillae, radish seed, kelp, poria, malt, semen coicis, nutmeg, *agastache rugosa*, and fructus amomi having undergone purification, cleansing, cutting, and grinding, for subsequent use;

(2) decocting: decocting twice a mixture obtained in step (1) with addition of water, to obtain a Chinese medicine liquid, operations of the twice decocting processes being as follows:

for the first time, adding water of 10 times the weight of the mixture obtained in the step (1), heating them for decocting and extracting the same, wherein timing was started when they were boiling, and after 1.5 hours of decoction and extraction, immediately feeding the medicine liquid through a pipeline filter by a pump into a stainless steel medicine liquid tank;

for the second time, adding water of 8 times the weight of the mixture obtained in the step (1), heating them for decocting and extracting the same, wherein timing was started when they were boiling, and after 1.5 hours of decoction and extraction, immediately feeding the medicine liquid through the pipeline filter by the pump into the stainless steel medicine liquid tank, and mixing it evenly with the medicine liquid obtained from the first time of decoction and extraction;

(3) concentrating: feeding the Chinese medicine liquid obtained in step (2) into a concentrator via a pipeline, to be concentrated into a thick paste, the concentration temperature being 75° C., and the relative density of the resulted thick paste being 1.45 under the temperature condition of 50° C.;

(4) wet granulating:

(4.1) dry blending: putting dextrin, maltodextrin, soluble starch, and aspartame into an efficient mixing granulator to be mixed and stirred for 15 minutes, to obtain a mixed excipient;

(4.2) sizing for the first time: adding the thick paste extracted in step (3) gradually to the mixed excipient, mixing and stirring the thick paste at cutting speed I and stirring speed I to granulate them to obtain a soft material, and sizing the soft material for the first time with a 12-mesh screen;

(4.3) drying: putting the sized particles obtained in step (4.2) into a boiling dryer to be dried, the temperature of the materials being kept at 78° C., and the moisture of the final materials being kept at 3.4%; (4.4) sizing for the second time: performing the second time of sizing by an oscillating machine with a 10-mesh screen;

(4.5) selecting particles: selecting particles with 10-60 meshes;

(5) packaging: bagging mixed qualified particles according to standard operation instructions of an automatic packaging machine, wherein packaging appearance and quantity was detected at any time, and adjustment was made in time in case of abnormalities, closing and storing the packaged particles in a clean container, with a product name, a lot number, quantity, date, etc. being marked for subsequent use, wherein a reference packaging quantity was 8 g per bag, and a packaging quantity limit was 8 g per bag ±5%.

EXAMPLE 4

A solid drink for regulating phlegm-dampness constitution included the following components of raw materials in parts by weight: kudzu vine root 50 parts, nutmeg 30 parts, fructus perillae 45 parts, radish seed 49 parts, dried tangerine peel 46 parts, poria 45 parts, fructus amomi 11 parts, malt 46 parts, agastache rugosa 29 parts, kelp 47 parts, semen coicis 36 parts, dextrin 80 parts, maltodextrin 63 parts, soluble starch 63 parts, and aspartame 0.4 parts.

A preparing method was as follows:

(1) preparing raw materials: mixing kudzu vine root, dried tangerine peel, fructus perillae, radish seed, kelp, poria, malt, semen coicis, nutmeg, agastache rugosa, and fructus amomi having undergone purification, cleansing, cutting, and grinding, for subsequent use;

(2) decocting: decocting twice a mixture obtained in step (1) with addition of water, to obtain a Chinese medicine liquid, operations of the twice decocting processes being as follows:

for the first time, adding water of 10 times the weight of the mixture obtained in the step (1), heating them for decocting and extracting the same, wherein timing was started when they were boiling, and after 1.5 hours of decoction and extraction, immediately feeding the medicine liquid through a pipeline filter by a pump into a stainless steel medicine liquid tank;

for the second time, adding water of 8 times the weight of the mixture obtained in the step (1), heating them for decocting and extracting the same, wherein timing was started when they were boiling, and after 1.5 hours of decoction and extraction, immediately feeding the medicine liquid through the pipeline filter by the pump into the stainless steel medicine liquid tank, and mixing it evenly with the medicine liquid obtained from the first time of decoction and extraction;

(3) concentrating: feeding the Chinese medicine liquid obtained in step (2) into a concentrator via a pipeline, to be concentrated into a thick paste, the concentration temperature being 73° C., and the relative density of the resulted thick paste being 1.33 under the temperature condition of 50° C.;

(4) wet granulating:

(4.1) dry blending: putting dextrin, maltodextrin, soluble starch, and aspartame into an efficient mixing granulator to be mixed and stirred for 15 minutes, to obtain a mixed excipient;

(4.2) sizing for the first time: adding the thick paste extracted in step (3) gradually to the mixed excipient, mixing and stirring the thick paste at cutting speed I and stirring speed I to granulate them to obtain a soft material, and sizing the soft material for the first time with a 12-mesh screen:

(4.3) drying: putting the sized particles obtained in step (4.2) into a boiling dryer to be dried, the temperature of the materials being kept at 72° C., and the moisture of the final materials being kept at 4.5%;

(4.4) sizing for the second time: performing the second time of sizing by an oscillating machine with a 10-mesh screen:

(4.5) selecting particles: selecting particles with 10-60 meshes;

(5) packaging: bagging mixed qualified particles according to standard operation instructions of an automatic packaging machine, wherein packaging appearance and quantity was detected at any time, and adjustment was made in time in case of abnormalities, closing and storing the packaged particles in a clean container, with a product name, a lot number, quantity, date, etc. being marked for subsequent use, wherein a reference packaging quantity was 8 g per bag, and a packaging quantity limit was 8 g per bag ±5%.

EXAMPLE 5

A solid drink for regulating phlegm-dampness constitution included the following components of raw materials in parts by weight: kudzu vine root 40 parts, nutmeg 24 parts, fructus perillae 40 parts, radish seed 40 parts, dried tangerine peel 40 parts, poria 40 parts, fructus amomi 8 parts, malt 40 parts, *agastache rugosa* 24 parts, kelp 40 parts, semen coicis 40 parts, dextrin 68 parts, maltodextrin 51 parts, soluble starch 51 parts, and aspartame 0.3 parts.

A preparing method was as follows:

(1) preparing raw materials: mixing kudzu vine root, dried tangerine peel, fructus perillae, radish seed, kelp, poria, malt, semen coicis, nutmeg, *agastache rugosa*, and fructus amomi having undergone purification, cleansing, cutting, and grinding, for subsequent use;

(2) decocting: decocting twice a mixture obtained in step (1) with addition of water, to obtain a Chinese medicine liquid, operations of the twice decocting processes being as follows:

for the first time, adding water of 10 times the weight of the mixture obtained in the step (1), heating them for decocting and extracting the same, wherein timing was started when they were boiling, and after 1.5 hours of decoction and extraction, immediately feeding the medicine liquid through a pipeline filter by a pump into a stainless steel medicine liquid tank;

for the second time, adding water of 8 times the weight of the mixture obtained in the step (1), heating them for decocting and extracting the same, wherein timing was started when they were boiling, and after 1.5 hours of decoction and extraction, immediately feeding the medicine liquid through the pipeline filter by the pump into the stainless steel medicine liquid tank, and mixing it evenly with the medicine liquid obtained from the first time of decoction and extraction;

(3) concentrating: feeding the Chinese medicine liquid obtained in step (2) into a concentrator via a pipeline, to be concentrated into a thick paste, the concentration temperature being 77° C., and the relative density of the resulted thick paste being 1.4 under the temperature condition of 50° C.

(4) wet granulating:

(4.1) dry blending: putting dextrin, maltodextrin, soluble starch, and aspartame into an efficient mixing granulator to be mixed and stirred for 15 minutes, to obtain a mixed excipient;

(4.2) sizing for the first time: adding the thick paste extracted in step (3) gradually to the mixed excipient, mixing and stirring the thick paste at cutting speed I and stirring speed I to granulate them to obtain a soft material, and sizing the soft material for the first time with a 12-mesh screen:

(4.3) drying: putting the sized particles obtained in step (4.2) into a boiling dryer to be dried, the temperature of the materials being kept at 76° C., and the moisture of the final materials being kept at 3.8%; (4.4) sizing for the second time: performing the second time of sizing by an oscillating machine with a 10-mesh screen;

(4.5) selecting particles: selecting particles with 10-60 meshes;

(5) packaging: bagging mixed qualified particles according to standard operation instructions of an automatic packaging machine, wherein packaging appearance and quantity was detected at any time, and adjustment was made in time in case of abnormalities, closing and storing the packaged particles in a clean container, with a product name, a lot number, quantity, date, etc. being marked for subsequent use, wherein a reference packaging quantity was 8 g per bag, and a packaging quantity limit was 8 g per bag ±5%.

EXPERIMENT EXAMPLE 1

Below is a Test of Effects of the Solid Drink for Regulating Phlegm-Dampness Constitution Prepared in Example 5 of the Present Invention.

Basic situation of cases: there were 120 cases of phlegm-dampness constitution, 60 males, and 60 females, among which the youngest was 13 years old, and the oldest was 66 years old. 40 cases suffered from repeated attacks of cough, excessive sticky and greasy phlegm or heavy and lumped phlegm, white in color or grayish, worsened when taking sweet and greasy food, physical lassitude, with white greasy tongue fur and soft-smooth pulse; 40 cases suffered from abdomen blockage discomfort, worsened especially when taking food, chest distress, dizziness, heavy body and drowsiness, nausea and vomiting, poor appetite and digestion, tastelessness in the mouth and hydroadipsia, with regular or unsolid bowel movement, white greasy tongue fur, and soft-smooth pulse; 40 cases suffered from head heaviness darkness, chest distress and nausea, vomiting and sputum, and reduced appetite and sleepiness, with white greasy tongue fur and soft-smooth pulse.

Usage and dosage: 8 g for each time, twice a day, dissolved in 200 ml of boiling water for administration.

Standards for Evaluating Efficacy:

Cured: clinical symptoms completely disappear, and normal life is resumed.

Taking effect: most of the symptoms disappear, with great improvements.

Effective: a small part of the clinical symptoms disappear, with gradual improvements of various physical signs.

Failed: no significant improvement on the symptoms is observed.

Statistics of results: 53 cases cured, taking effect for 27 cases, effective for 30 cases, failed for 10 cases, that is, effective for 91 cases in total, with the overall effective rate of 91.67%.

EXPERIMENT EXAMPLE 2

Sensory Evaluation

The solid drink prepared in Examples 1 to 5 was mixed with boiling water and then taken as test groups, and the mixed medicine liquid after the two times of decoction prepared and obtained in step (2) in the processing process of Example 5 as a control group. Samples of the test groups and the control group were set to have three repetitions. 20 professional sensory evaluators performed the sensory evaluation. The sensory evaluating and scoring standards are shown in Table 1, and the sensory evaluating results are shown in Table 2.

TABLE 1

| Sensory Evaluating and Scoring Standards | | |
| --- | --- | --- |
| Item | Sensory Evaluation | Score |
| Color | dark | 1 |
|  | suitable | 5 |
|  | light | 1 |
| Odor | strong Chinese medicine smell | 1 |
|  | slight Chinese medicine smell | 3 |
|  | medicine fragrance | 5 |
|  | relatively light | 3 |
|  | light | 1 |
| Taste | bitter | 1 |
|  | relatively bitter | 3 |
|  | fragrant and sweet | 5 |
|  | relatively sweet | 3 |
|  | too sweet | 1 |
| Smoothness | smooth and lubricated | 5 |
|  | sense of particles | 3 |

TABLE 1-continued

Sensory Evaluating and Scoring Standards

| Item | Sensory Evaluation | Score |
|---|---|---|
| | sense of scratching throat | 1 |
| | hard to swallow | 0 |
| Overall | bad | — |
| Evaluation | ordinary | — |
| | good | — |

TABLE 2

Sensory Evaluating Results of Solid Drink

| | | Control | Test Groups | | | | | |
|---|---|---|---|---|---|---|---|---|
| Item | | Group | Example 1 | Example 2 | Example 3 | Example 4 | Example 5 | Mean |
| Sensory Evaluate on (score) | Color | 39 | 92 | 97 | 94 | 92 | 96 | 94.2 |
| | Odor | 48 | 93 | 94 | 97 | 95 | 95 | 94.8 |
| | Taste | 33 | 94 | 96 | 93 | 95 | 94 | 94.4 |
| | Smoothness | 70 | 92 | 95 | 93 | 94 | 94 | 93.6 |
| | Mean | 47.5 | 92.75 | 95.5 | 94.25 | 94 | 94.75 | 94.25 |
| Overall Evaluation (number of person) | Good | 7 | 20 | 18 | 20 | 19 | 19 | 19.2 |
| | Ordinary | 6 | 0 | 2 | 0 | 1 | 1 | 0.8 |
| | Bad | 7 | 0 | 0 | 0 | 0 | 0 | 0 |

It can be seen from the above test results that the mean scores of the color, odor, taste, and smoothness of the solid drink prepared in Examples 1 to 5 evaluated by the 20 professional sensory evaluators are higher than the scores of the control group. The results show that the solid drink provided in the present invention is greatly improved in the odor and taste over the medicine liquid obtained after decocting a Chinese medicine decoction piece, moreover, the sweet taste is added, and the taste and the smoothness are both substantially improved, quite suitable for daily drinking.

EXPERIMENT EXAMPLE 3

Animal Experiment

In order to manifest that a composition prepared in the present invention has unpredictable technical effects to the phlegm-dampness constitution, rats were fed with high-fat diet, and lived in humid environment (85%-90% of humidity, and 18-20° C. of temperature) for 12 weeks, to create models of phlegm-dampness syndrome. The specific experiment is as follows:

1. Experiment Animals:
SD rats, half males and half females, with a body weight of 200±10 g.

2. Experiment Supply
Particles of the solid drink prepared in Examples 1-5 of the present application;
High-fat diet.

3. Experiment Process
3.1 Creating Models
The rats were randomly divided into a blank control group, a model group, and 5 experiment groups of Examples 1-5. The rats of the blank control group were fed routinely, and ate and drank freely, while the rats of the other groups were fed with the high-fat diet from the beginning of the experiment, and lived in a humid environment (85%-90% of humidity, and 18-20° C. of temperature) continuously for 12 weeks, then the rats were subjected to intraperitoneal injection of 0.2 mL/100 g of 3% pentobarbital sodium to anaesthetize, and blood was taken from the ventral abdominal artery.

3.2 Experiment Grouping
The rats were randomly divided into 7 groups: the blank control group, the model group, and 5 experiment groups, 20 rats in each group; the rats of the experiment groups were respectively orally administered with the particles of the solid drink prepared in Examples 1-5 of the present application, and the rats of the blank group were orally administered with an equal amount of normal saline.

3.3 Statistical Manner
The statistics were made with the SPSS12.0 software, and one-way analysis of variance was used in the method. The analysis of variance was used for comparison among groups. The difference of $P<0.05$ indicates statistical significance.

4. Behavior Observation
Monitoring of general conditions: observing the situations of spirit, activity, etc. of the model animals, and scoring according to the specific representation by consulting the scoring table of Table 3. The scoring results are shown in Table 4.

TABLE 3

| Score | Spirit Situation | Skin and Hair | Color of Ear and Tail | Excrement |
|---|---|---|---|---|
| 0 | Lively and active | Tight connection between skin and fat, flexible skin, and bright and silky hair | Ruddy and lustrous | Dry and shaped-up |
| 1 | Slightly slow in reacting, with reduction of locomotor activities | Slightly loose skin, with reduced tension, dry yellow hair without lustre | Reddish and lacking lustre | Gummy, soft, and tangible |
| 2 | Tired and lazy, sluggish | Loose skin, more fat, dry or tangled and wavy hair | Slightly white and | Unshaped, loose, and |

TABLE 3-continued

| Score | Spirit Situation | Skin and Hair | Color of Ear and Tail | Excrement |
|---|---|---|---|---|
| | | | lacking lustre | stinky |
| 3 | Inert, with decreased antagonistic behavior | Loose skin, obesity, yellow and sparse hair, with loss of hair | Pale or cyan | Loose, green-brown, gummy and soft, and fetid |

TABLE 4

Observation Table of Biological Representation of Rats of Various Experiment Groups

| Group | n | Score |
|---|---|---|
| Blank Group | 20 | 1.32 ± 0.49 |
| Model Group | 20 | 4.78 ± 0.97** |
| Example 1 | 20 | 1.38 ± 0.36## |
| Example 2 | 20 | 1.51 ± 0.42## |
| Example 3 | 20 | 1.48 ± 0.71## |
| Example 4 | 20 | 1.44 ± 0.65## |
| Example 5 | 20 | 1.41 ± 0.69## |

Notes:
compared with the blank group,
**P < 0.01, and compared with the model group,
P < 0.01

It can be seen from Table 4 that the experiment results of the scoring of the biological representation of the rats of various groups show that the rats of the blank group were lively and active, and quick-witted; the rats of the model group seemed tired and lazy, weary in spirit, and sluggish in action, with obese body, gradually took less food, with slightly white tail and nose lacking lustre, loose and stinky excrement, of which the score of biological representation was significantly increased compared with the blank group (P<0.01); compared with the model group, the rats of the 5 experiment groups of the present application reacted slightly slowly, with reduction of locomotor activities, slightly loose and soft skin, reddish tail and nose lacking lustre; dry and shaped-up excrement, of which the score of biological representation was significantly decreased (P<0.01).

5. Detection of Senrum TC, TG, HDLC, LDLC, and VLDLC

Blood was taken from the ventral abdominal artery, and after standing for 4 h, underwent centrifugation at 6000 rpm for 5 min, and then the serum was taken, and subjected to automatic biochemical detection for five indexes, namely, total cholesterol (TC), triglyceride (TG), high density lipoprotein cholesterol (HDLC), low density lipoprotein cholesterin (LDLC), very low density lipoprotein cholesterol (VLDLC).

The experiment results show that compared with the blank group, the rats of the model group had significantly increased contents of serum TC, HDLC, LDLC, and VLDLC and significantly decreased TG. Compared with the model group, the five experiment groups of the present application have significantly decreased TC, HDLC, LDLC, and VLDLC and significantly increased TG.

The experiment results show that the particles of the solid drink of Examples 1-5 of the present application have good regulating and curing effects to the phlegm-dampness syndromes.

The foregoing only describes preferred examples of the present invention and is not intended to limit the present invention. For a person skilled in the art, various modifications and variations may be made to the present invention. Any modifications, equivalent replacements, improvements, etc., made within the spirit and principle of the present invention, should be covered by the scope of protection of the present invention.

What is claimed is:

1. A solid drink for regulating phlegm-dampness constitution, comprising: a decocted solution of a mixture of raw materials in water; wherein, the mixture of raw materials comprises kudzu vine root 25-60 parts by weight, nutmeg 13-35 parts by weight, fructus perillae 30-50 parts by weight, radish seed 34-53 parts by weight, dried tangerine peel 28-55 parts by weight, poria 27-52 parts by weight, fructus amomi 4-15 parts by weight, malt 26-50 parts by weight, *agastache rugosa* 14-33 parts by weight, kelp 24-51 parts by weight, semen coicis 22-40 parts by weight, dextrin 50-90 parts by weight, maltodextrin 38-70 parts by weight, soluble starch 35-70 parts by weight, and aspartame 0.1-0.5 parts by weight.

2. The solid drink of claim 1, wherein, the kudzu vine root is 30-50 parts by weight, the nutmeg is 18-30 parts by weight, the fructus perillae is 35-45 parts by weight, the radish seeds are 37-49 parts by weight, the dried tangerine peel is 33-46 parts by weight, the poria is 33-45 parts by weight, the fructus amomi is 6-11 parts by weight, the malt is 32 -46 parts by weight, the *agastache rugosa* is 17-29 parts by weight, the kelp is 31-47 parts by weight, the semen coicis is 29-36 parts by weight, the dextrin is 60-80 parts by weight, the maltodextrin is 45-63 parts by weight, the soluble starch is 45-63 parts by weight, and the aspartame is 0.2-0.4 parts by weight.

3. The solid drink of claim 1, wherein, the kudzu vine root is 40 parts by weight, the nutmeg is 24 parts by weight, the fructus perillae is 40 parts by weight, the radish seeds are 40 parts by weight, the dried tangerine peel is 40 parts by weight, the poria is 40 parts by weight, the fructus amomi is 8 parts by weight, the malt is 40 parts by weight, the *agastache rugosa* is 24 parts by weight, the kelp is 40 parts by weight, the semen coicis is 40 parts by weight, the dextrin is 68 parts by weight, the maltodextrin is 51 parts by weight, the soluble starch is 51 parts by weight, and the aspartame is 0.3 parts by weight.

4. A method for processing the solid drink for regulating phlegm-dampness constitution according to claim 1, comprising the following steps:
(1) preparing raw materials: mixing kudzu vine root, dried tangerine peel, fructus perillae, radish seed, kelp, poria, malt, semen coicis, nutmeg, *agastache rugosa*, and fructus amomi having undergone purification, cleansing, cutting, and grinding, to form a mixture;
(2) decocting: decocting twice the mixture obtained in step (1) with addition of water, to obtain a Chinese medicine liquid;

(3) concentrating: feeding the Chinese medicine liquid obtained in step (2) into a concentrator via a pipeline, to be concentrated into a thick paste;

(4) wet granulating: mixing and stirring dextrin, maltodextrin, soluble starch, and aspartame to obtain a mixed excipient, and adding the thick paste obtained in step (3) to the mixed excipient, then stirring and granulating them.

5. The method of claim 4, wherein operations of the twice decocting processes in the step (2) includes:

for the first time, adding water of 10 times the weight of the mixture obtained in the step (1), heating them for decocting and extracting the same, wherein a timing is started when they are boiling, and after 1.5 hours of decoction and extraction, immediately feeding a medicine liquid through a pipeline filter by a pump into a stainless steel medicine liquid tank;

for the second time, adding water of 8 times the weight of the mixture obtained in the step (1), heating them for decocting and extracting the same, wherein timing is started when they are boiling, and after 1.5 hours of decoction and extraction, immediately feeding the medicine liquid through the pipeline filter by the pump into the stainless steel medicine liquid tank, and mixing it evenly with the medicine liquid obtained from the first time of decoction and extraction.

6. The method of claim 4, wherein a concentration temperature in the step (3) is 70-80° C., and a relative density of the resulted thick paste is 1.2-1.5 under a temperature condition of 50° C.

7. The method of claim 4, wherein the wet granulating in the step (4) comprises the following steps:

(4.1) dry blending: putting dextrin, maltodextrin, soluble starch, and aspartame into an efficient mixing granulator to be mixed and stirred for 15 minutes, to obtain the mixed excipient;

(4.2) sizing for the first time: adding the thick paste extracted in step (3) gradually to the mixed excipient, mixing and stirring the thick paste at cutting speed I and stirring speed I to granulate them to obtain a soft material, and sizing the soft material for the first time to obtain size particles;

(4.3) drying: putting the sized particles obtained in step (4.2) into a boiling dryer to be dried;

(4.4) sizing for the second time: performing the second time of sizing by an oscillating machine.

8. The method of claim 7, wherein a 12-mesh screen is used in the first time of sizing, and a 10-mesh screen is used in the second time of sizing.

9. The method of claim 7, wherein in the drying process of step (4.3), a temperature of materials is kept at 70-80° C., and a moisture of final materials is kept below 5%.

10. The method of claim 7, further comprising a step of selecting particles performed after the second time of sizing, to select particles with 10-60 meshes.

* * * * *